US006825655B2

(12) United States Patent
Minchole et al.

(10) Patent No.: US 6,825,655 B2
(45) Date of Patent: Nov. 30, 2004

(54) METHOD AND ARRANGEMENT FOR DETECTING CHANGES OF A MAGNETIC RESPONSE IN MAGNETIC PARTICLES

(75) Inventors: Ana Minchole, Zaragoza (ES); Andrea P. Astalan, Gothenburg (SE); Christer Johansson, Gothenburg (SE); Kerstin Lagerwall-Larsson, Gothenburg (SE); Anatol Krozer, Gothenburg (SE)

(73) Assignee: Imego AB, Gotebord (SE)

( * ) Notice: Subject to any disclaimer, the term of this patent is extended or adjusted under 35 U.S.C. 154(b) by 0 days.

(21) Appl. No.: 10/331,150

(22) Filed: Dec. 30, 2002

(65) Prior Publication Data

US 2003/0169032 A1 Sep. 11, 2003

Related U.S. Application Data

(63) Continuation-in-part of application No. 10/230,360, filed on Aug. 29, 2002.
(60) Provisional application No. 60/316,040, filed on Aug. 31, 2001.

(51) Int. Cl.[7] .......................... G01N 27/72; G01N 27/74
(52) U.S. Cl. ....................... 324/204; 324/233; 324/226; 436/526; 204/557; 422/68.1
(58) Field of Search .......................... 73/61.41; 324/201, 324/204, 226, 232, 233, 234, 236, 239, 243, 248; 422/68.1; 436/526; 204/557

(56) References Cited

U.S. PATENT DOCUMENTS

| | | | | |
|---|---|---|---|---|
| 3,773,684 A | * | 11/1973 | Marks | 252/583 |
| 6,027,946 A | | 2/2000 | Weitschies et al. | 436/526 |
| 6,437,563 B1 | * | 8/2002 | Simmonds et al. | 324/239 |
| 6,485,985 B1 | * | 11/2002 | Weitschies et al. | 436/526 |
| 6,597,176 B2 | * | 7/2003 | Simmonds et al. | 324/326 |

OTHER PUBLICATIONS

Copy of International Search Report for International Application No. PCT/SE 02/00964, mailed Sep. 4, 2002, 3 pages.
M. Meza, "Applications of Magnetic Particles In Immunoassays", Chapter 22, *Scientific and Clinical Applications Of Magnetic Carriers*, (Urs Häfeli et al. eds., Plenum Press, 1997), pp. 303–309.
Berkowitz, A.E., and Kneller, E., "Magnetism and Metallurgy", vol. 1, Academic Press, New York, )1969), pp. 366–469.
Bean, C.P. and Livingston, J.D., "Superparamagnetism", *J. Appl. Phys*, 30, (1959), pp. 120S–129S.
Neel, L., *Academie Des Sciences*, 228, (1949), pp. 664–666.
Brown Jr., W.F., "Thermal Fluctuations Of A Single–Domain Particle", *J. Appl. Phys.*, vol. 34, (Apr. 1963), pp. 1319–1320.
Fannin, P.C. et al., "The Measurement Of The Frequency Dependent Susceptibility Of Magnetic Colloids", *J. Magnetism and Magnetic Materials*, 72, (1988), pp. 95–108.
Kötitz, R., et al., "Superconducting Quantum Interference Device–Based Magnetic Nanoparticle Relaxation Measurement As A Novel Tool For The Binding Specific Detection Of Biological Binding Reactions (Abstract)", *J. Appl. Phys.*, 81(8), 4317, (Apr. 15, 1997).

(List continued on next page.)

*Primary Examiner*—Jay Patidar
(74) *Attorney, Agent, or Firm*—Sterne Kessler Goldstein & Fox PLLC

(57) ABSTRACT

A method for detecting changes of magnetic response of at least one magnetic particle provided with a external layer in a carrier fluid, comprising measuring the characteristic rotation time of the magnetic particle with respect to the external layer, and measuring Brownian relaxation in the carrier fluid under the influence of an external alternating magnetic field. The method implies that upon modification of the effective volume of the particle or its interaction with the carrier fluid, a hydrodynamic volume of the particle changes, which implies a change of the frequency ($f_{max}$) at which an out of phase component of the magnetic susceptibility has its maximum.

58 Claims, 7 Drawing Sheets

OTHER PUBLICATIONS

Kötitz, R., et al., "SQUID Based Remanence Measurements For Immunoassays", *IEEE Transactions On Applied Superconductivity*, vol. 7, No. 2, (1997), pp. 3678–3681.

Enpuku, K., et al., Application of High $T_c$ SQUID Magnetometer To Biological Immunoassays, *IEEE Transactions On Applied Superconductivity*, vol. 11, No. 1, (2001), pp. 661–664.

Grossman, H.L., et al., "Rapid, Sensitive, Selective Detection Of Pathogenic Agents Using A SQUID Microscope", *Eurosensors XIV*, (Aug. 27–30, 2000), pp. 137–138.

Grüttner C., et al., "Preparation And Characterization Of Magnetic Nanospheres For In Vivo Application", *Scientific and Clinical Applications of Magnetic Carriers*, Plenum Pres, New York, (1997), pp. 53–67.

Horowitz, P. and Hill, W., "The Art Of Electronics", *Cambridge University Press*, $2^{nd}$ Ed., (1989).

Parzen, B., "Design Of Crystal And Other Harmonic Oscillators", *Wiley–Interscience Publication, John Wiley & Sons*, (1983).

* cited by examiner

METHOD AND ARRANGEMENT FOR DETECTING CHANGES OF A MAGNETIC RESPONSE IN MAGNETIC PARTICLES

CROSS-REFERENCE TO RELATED APPLICATIONS

This application is a continuation-in-part of U.S. patent application Ser. No. 10/230,360 filed Aug. 29, 2002, which claims the benefit of U.S. Provisional Patent Application 60/316,040, filed Aug. 31, 2001.

FIELD OF THE INVENTION

The present invention relates to an arrangement for detecting changes of a magnetic response with at least one magnetic particle provided with an external layer in a carrier fluid, thus the method comprises using a measuring method comprising measuring the characteristic rotation time of said magnetic particle with respect to said external layer, which measuring method involves measuring Brownian relaxation in said carrier fluid under the influence of an external alternating magnetic field.

BACKGROUND

Magnetic spherical particles with a diameter of less than about 20 nm are magnetic mono domains both in a magnetic field and in the zero field. A particle being a magnetic mono domain means that the particle only contains one magnetization direction.

Depending on the size, geometry, temperature, measurement time, magnetic field and material of the particles, they can either be thermally blocked or super paramagnetic. The direction of the magnetization for thermally blocked particles are oriented in a specific direction in the magnetic particle in proportion to the crystallographic orientation of the particle, and "locked" to this direction, meanwhile studying the particle system. Under influence of an external magnetic field, the entire particle physical rotates so that their magnetization directions gradually partly coincide with the direction of the external added field.

Small magnetic particles can be manufactured in a number of materials, for example magnetite ($Fe_3O_4$), maghemite ($\gamma$-$Fe_2O_3$), cobalt doped iron oxide or cobalt iron oxide ($CoFe_2O_4$). Other magnetic materials, especially (but not exclusively) rare earth metals (for example ytterbium or neodymium), their alloys or compounds containing rare earth metals, or doped magnetic (element) substances can also be possible. The sizes of the particles that can be produced from about 3 nm to about 30 nm. The final size in this process depends on a number of different parameters during manufacturing.

Magnetization in small particles can relax in two different ways, via Néelian relaxation or on the other hand via Brownian relaxation. These relaxation phenomena are related to particles with a magnetic arranged structure. They should not be mistaken for nuclear magnetic (NMR) resonance phenomenon's, the latter describes resonances within the atomic nucleus. The latter resonance phenomena have resonance frequencies typically within the GHz-range unlike resonance frequencies for the phenomenon considered in this patent, which are in the range of a few Hz to several MHz.

Néelian Relaxation

In Néelian relaxation the magnetization in the particle relax without the particle physical rotating (no thermal blocking). The relaxation period for this kind of relaxation strongly depends on size, temperature, material and (at high particle concentrations) on the magnetic interaction between the particles. For this relaxation being available the magnetization direction in the particle has to change direction fast in time, the particles have to be super-paramagnetic. Néelian relaxation period in the zero field can be described according to the equation below:

$$\tau_N = \tau_0 e^{\frac{KV}{kT}}$$

wherein $\tau_0$ is a characteristic relaxation period, K is the magnetic anisotropic constant, V magnetic particle volume, k is Boltzman's constant and T temperature.

Brownian Relaxation

In the Brownian relaxation, the magnetization-direction rotates when the particle physically rotates. For this relaxation being available the magnetization has to be locked in a specific direction in the particle, and the particle has to be thermal blocked. The relaxation period for Brownian relaxation depends on hydrodynamic particle volume, viscosity of the carrier fluid in which the particles are dispersed in, contact between the surface of the particle and the fluid layer nearest it's surface (Hydrophobic and hydrophilic respectively). The Brownian relaxation can approximately be described according to the equation below:

$$\tau_B = \frac{3V_H \eta}{kT}$$

wherein $V_H$ is the hydrodynamic volume for the total particle (inclusive of the polymer layer), $\eta$ viscosity for the surrounding carrier fluid, k is Boltzmann's constant and T is the temperature. The above derivation assumes a perfect wetting (hydrophilic) has been assumed and a constant rotation speed (the initial approximation has been neglected).

The Brownian relaxation period accordingly depends on the (effective) size of the particle and the environmental effect on the particle. To discern if a particle shows Brownian relaxation or Néelian relaxation you can among other things study whether external influences (for example a different fluid viscosity, temperature changes, applied static magnetic field) changes the relaxation period.

You can also study the phenomenon in the frequency domain, which involves determining the resonance frequencies regarding the particle system. These can be obtained for example by means of AC-susceptometry (for Brownian relaxation some Hz till kHz region and for Néelian relaxation typically in the MHz region).

As is apparent from the above, a Brownian movement (Brownian relaxation) depends, among other things on the volume of the particle: the lager particle the longer relaxation period that is and the smaller the movement of the particle gets. Relaxations periods for particles lager than about 1 $\mu$m are much longer than 1 second, which in practice means a negligible movement. Even these particles, though can be used at detection. Larger particles can, however, show other types of relaxations wherein the inertia of the particles and visco-elastic characteristics of the carrier fluid must be included for a sufficient data interpretation.

Frequency Susceptibility

The magnetization for a particle system in an alternating magnetic field can be described according to:

$$M = \chi H = (\chi' - j\chi'')H$$

wherein M is the magnetization, H the alternating external magnetic field, $\chi$ is the frequency dependent complex susceptibility consisting of an in phase component (real part), $\chi'$, and one out of phase component (imaginary part), $\chi''$. The in phase and the out of phase components for a magnetic particle system can approximately be described as:

$$\chi' = \frac{\chi_0}{1+(2\pi f\tau)^2}$$

$$\chi'' = \frac{\chi_0(2\pi f\tau)}{1+(2\pi f\tau)^2}$$

wherein $\chi_0$ is the DC value of the susceptibility and $\tau$ is the relaxation period for magnetic relaxation.

Assuming a particle system with varying particle sizes wherein some of the particles go through Brownian relaxation (the larger particles) and some Néelian relaxation (the smaller particles) you obtain a magnetic response contribution from both the relaxation processes depending on the frequency range AC field. FIG. 1 shows schematically the total magnetic response as a function of the frequency for the particle system that shows both Brownian and Néelian relaxation. The upper curve (dashed line) in the figure is the real part of the susceptibility and the lower curve (continuous line) is the imaginary part of the susceptibility. The maximum for the imaginary part at lower frequencies is from the Brownian relaxation and the maximum at high frequencies is from the Néelian relaxation. The total magnetic response is the sum of the contributions from both the processes for both real and imaginary part of the susceptibility.

For this application only the Brownian relation is interesting, therefore the discussion is concentrated at these lower frequencies.

For a particle system with particles showing Brownian relaxation with only one hydrodynamic volume you obtain a maximum in the out of phase component ($\chi''$, the imaginary part of the complex susceptibility) at a frequency according to:

$$f_{max} = \frac{1}{2\pi\tau_B} = \frac{kT}{6\pi V_H \eta}$$

Around this frequency, $f_{max}$, the real part of the susceptibility, $\chi'$, will decline very much while the imaginary part of the susceptibility, $\chi''$, will exhibit a maximum. The value of $\chi''$ at the maximum (B in the FIG. 1) is among other things a measure of the number of particles that goes through Brownian relaxation while the level of the magnetic response for $\chi'$ (C in FIG. 1) after the maximum in $\chi''$ is a measure of the total number of particles that still magnetically can follow the applied AC field (in this case particles that goes through Néelian relaxation). At sufficient low frequencies all particles can magnetically follow the AC field, that is, the real part of the susceptibility at these low frequencies (A in FIG. 1) is a measure of the total number of particles. The contribution from the Brownian particles can then be quantified as the difference between the total contribute, A and the Néelian contribution, C (D in FIG. 1). At higher frequencies, a new maximum is obtained in $\chi''$ as a result of the Néelian relaxation (E in FIG. 1). The comparison between these two values is therefore a measure of the concentration of particles in a sample that goes through the Brownian relaxation, which is of interest for this application. The width of the maximum of $\chi''$, $\delta f_{max}$ (and the speed of the subside of $\chi'$) is a measure of energy dissipation due to the fluids repercussion on the particles (the friction).

The friction vary with (above all) the spreading in the hydrodynamic volume between the particles as a particle population in a sample can show., but also depends partly also on statistical (temperature dependent) fluctuations.

By measuring susceptibility, the Brownian relaxation and the energy dissipation, one can determine the total concentration of particles, the degree of particles that goes through Brownian relaxation in this particle population, the mean size of a particle in a carrier fluid and the spreading in particle volumes.

Magnetic particles have earlier been used as carrier of bio-molecules or antibodies for measuring changes in their magnetic response. In these methods, the particles are either bound to a fixed surface or the particles are aggregated. One measures how the magnetic resonance decrease with time after the particle system is magnetized, see R. Kötitz, T. Bunte, W. Weitschies, L. Trahms, Superconducting quantum interference device-based magnetic nanoparticle relaxation measurement as a novel tool for the binding specific detection of biological binding reactions, J. Appl. Phys., 81, 8, 4317, 1997, or one measures the magnetic response when an external magnetic field is applied over the magnetic particles, see K. Enpuku, T. Minotani, M. Hotta, A. Nakohado, Application of High $T_c$ SQUID Magnetometer to Biological Immunoassays, IEEE Transactions on Applied Superconductivity, Vol. 11, No. 1, 661–664, 2001. In performing these measurements, one distinguishes between the Néelian relaxation and the Brownian relaxation. The measurements are performed with a totally different technique then that used for the present invention, so called SQUID-technique that requires the use of cryofluids and advanced electronics. H. L. Grossman, Y. R. Chemla, Y. Poon, R. Stevens, J. Clarke, and M. D. Alper, Rapid, Sensitive, Selective Detection of Pathogenic Agents using a SQUID Microscope, Eurosensors XIV, 27–30, 2000, also uses antibody cased magnetic nanoparticles for determining specific target molecules, but combines this with the SQUID technology—that is, with a superconducting detector.

There are three substantially differences between the procedure according to present invention and the above mentioned methods:

(i) the physical principles behind the measurements according to the invention are different from earlier performances when others have chosen to measure in time/period domains instead of in frequency domains as shown in this case, and also that the it is necessary to "pre-magnetizes" the particle system.

(ii) The method of measurement that many uses for measuring is constructed from a very sensitive, but expensive and complicated technology,—namely the SQUID technology.

(iii) The invention is based on that the agglomeration of the particles. This is accomplished through providing the particles with a surface having characteristics that prevent agglomerations from being formed. For example, monoclonal antibodies reacting specifically with the substance to be analyzed can cover the surface of the particles. According to known techniques, bio molecules with multiple ways of bonding have been analyzed.

In Kötitz, H. Matz, L. Trahms, H. Koch, W. Weitschies, T. Rheinlander, W. Semmler, T. Bunte, SQUID based remanence measurements for immunoassays, IEEE Transactions on Applied Superconductivity, vol. 7, No. 2, 3678–81, 1997, the Brownian relaxation in a system of magnetic nanoparticles has also been studied. They have been using magnetic balls covered with biotin. To this system they have added different amounts of avidin. When avidin has 4 bonding places to biotin, avidin-including agglomerate is created. In the present method, the molecule 1 and molecule 2 are chosen in such a way that no agglomerate is created. For example, monoclonal antibodies (molecule 1) can be bonded to the magnetic ball. This monoclonal antibody bonds to a specific etipop on the target molecule, which leads to prevention of agglomerate (FIG. 9).

Yet, another thing that distinguish the method according to the invention and similar methods is that in this case how the frequency dependent of the magnetic response is changed at different measurement frequencies using a relatively simple measuring arrangement. What further distinguishes the present method is that, according to the invention different bio-molecules or antibodies are bonded to the particle surface that changes the hydrodynamic volume. According to earlier methods particles are bond to a fixed surface or the particles are aggregated.

U.S. Pat. No. 6,027,946 describes a process for magnetorelaxometric quantitative detection of analyte in the fluid and solid phase, substances for magnetorelaxometric detection of analyses and immuno-magnetography. The process uses SQUID technique and both the device and the method differ from the present invention.

BRIEF DESCRIPTION OF THE INVENTION

The invention relates to detecting changes in the magnetic response of the magnetic particles that shows the Brownian relaxation in a carrier fluid (for example water or a suitable buffer fluid, or another fluid suitable for the bio-molecules that are the final target for the detection) under influence of an external AC-magnetic field. Upon modification of the efficient volume of the particles or their interaction with the surrounding fluid, for example when bio-molecules or antibodies are bond on their surfaces, the hydrodynamic volume of respective particles will be changes (increase) which involves a change (reduction) of the frequency, $f_{max}$, wherein the out of phase component of the magnetic susceptibility is at a maximum.

Hence, the initially mentioned method comprises use of a method further involving, upon modification of the effective volume of the particle or its interaction with the carrier fluid, a change in the hydrodynamic volume of the particle, which implies a change of the frequency where an out of phase component of the magnetic susceptibility is at a maximum. The measurement is actually a relative measurement in which changes in a modified particle system are compared with an original system. At least two sample containers and two detector coils are used for the measurement. Preferably, an oscillator circuit at a frequency is used, that frequency being the resonance frequency, wherein the detector coils are placed as a frequency-determining element in the oscillator circuit so that they are out of phase with each other. The frequency change and/or effect or the amplitude of the oscillations from the oscillation circuit over the coils is therefore measured.

An external oscillator/frequency generator can be arranged, in which the coils are in an alternating bridge so that the difference between both detector coils are measured, and so that the phase difference between the output current and/or voltage of the frequency generator and a current/voltage over the bridge is measured. In this case an amplitude difference between the oscillator output current/voltage can be measured and compared with an amplitude of the current/voltage in the bridge. The measurement is accomplished at one or several different frequencies.

A noise source can be used as well and that the response of the system can be analyzed by means of a FFT (Fast Fourier Transform) analysis of an output signal.

According to one embodiment, the signal difference is set to zero between the coils, which is done through mechanically adjusting position of the respective sample containers, and alternatively changing the position of the respective detection coils so that the difference signal is minimized. The zero setting can be achieved by minimizing the signal through adding a determined amount of a magnetic substance in one of the spaces wherein the sample containers are placed, so that the substance creates an extra contribution to the original signal that therefore can be set to zero. The magnetic substance shows substantially zero magnetic loss (imaginary part=0) and that the real part of the susceptibility is constant in the examined frequency range.

The method is preferably but not exclusively used in analysis instruments for analyzing different bio-molecules or other molecules in fluid. The molecules, comprises one or several proteins in a fluid solution, such as blood, blood plasma, serum or urine. The analysis (molecule 2) can be connected to the particle through interaction with a second molecule (molecule 1), which is connected to the particle before the analysis starts. Molecules that can be integrated specifically which each other can comprise one or more of antibody—antigen pairs, receptor—hormone pairs, two complementary single strings of DNA and enzyme—substrate/enzyme—inhibitor pairs.

According to a preferred embodiment, the surface of the magnetic particle is modified through covering the surface with one or more of dextrane, with alkanethiols with suitable end groups or with some peptides. The dextrane surface (or another suitable intermediate layer) can then be bonded to a first molecule, for example an antibody, be bond by means of, for example cyanobromide activation or carboxyl acid activation.

The invention also relates to an arrangement for performance of a method for detection of changes in the magnetic response of at least one magnetic particle provided with an external layer in a carrier fluid, the method comprising measuring the characteristic rotation period of the magnetic particles with respect to the agitation of the external layer. The arrangement comprises at least two substantially identically detection coils connected to detection electronics and sample containers for absorbing carrier fluid. An excitation coil can surround the detection coils and sample containers for generation of a homogeneous magnetic field at the sample container. According to one embodiment, the excitation coil, measurement coils and sample container are placed concentrically and adjusted around its vertical center axis. The arrangement can furthermore comprise an oscillator system wherein the detection coils constitutes the frequency-determining element in an oscillator circuit. The coils are arranged in the oscillator return coil. The respective coils that surround the samples are electrically phase shifted versus each other so that the resonance frequency is determined from the difference between the inductance and the resistance of the respective coil. The coils are placed in an AC-bridge. Additionally, an operation amplifier can be arranged to subtract two voltages from each other.

The arrangement comprises a phase locking circuit in one embodiment. In another embodiment the arrangement comprises oscillator/frequency generator signal to generate a time variable current to excite the coils by means of white noise. Frequency-depending information is received through an FFT-filtering of the response.

The inventions also relates to a method of determining an amount of molecules in a carrier fluid containing magnetic particles, where the determination may comprise the steps of:

A. providing the magnetic particles with a layer, which interacts/reacts with the substance to be analyzed;
B. compounding the magnetic particles with a sample to be analyzed with respect to molecules,
C. filling a sample container with the fluid being prepared according to step B,
D. placing sample container in the detection system,
E. applying an external measure field over the sample with a certain amplitude and frequency,
F. measuring up the magnetic response (both in phase and out of phase components) at this frequency,
G. changing frequency and executing the measurement according to steps D and E,
H. analyzing the result through determining a Brownian relaxation period from in phase and out of phase components through using data in the examined frequency interval.

The method further involves determining the frequency shift (for same value of in phase and out of phase components) at different frequencies. The molecule consists of a bio molecule.

BRIEF DESCRIPTION OF THE DRAWING

In the following, the invention will be described with respect to various embodiments and with references to the enclosing drawings, in which.

DETAILED DESCRIPTION OF THE PREFERRED EMBODIMENT

Figure 3:
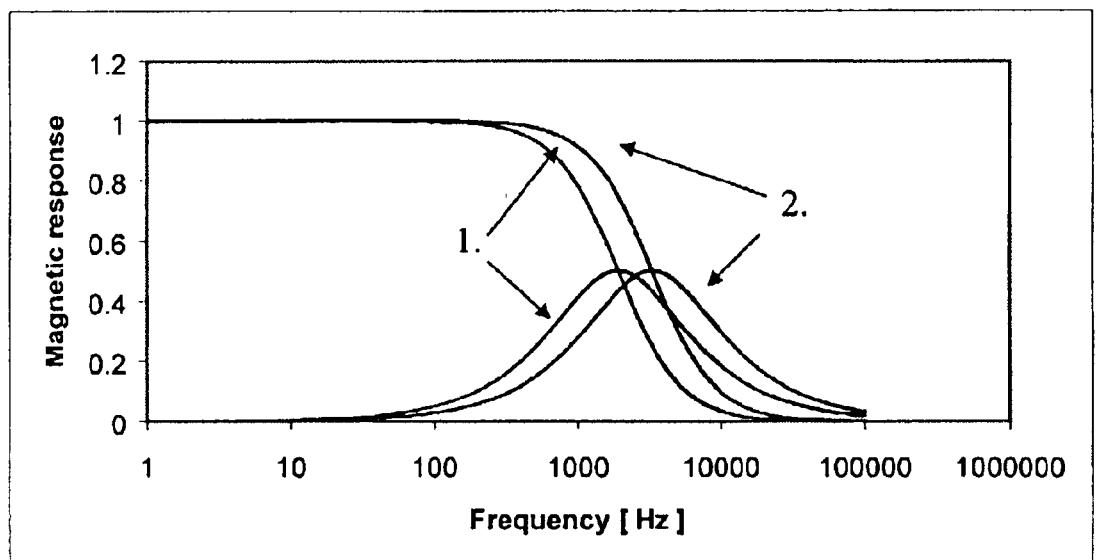
FIG. 3 shows how in phase and out of phase components of the magnetic susceptibility vary with the frequency at room temperature for two different hydrodynamic diameters.

FIG. 3 shows how in phase and out of phase components of the magnetic susceptibility vary with frequency at room temperature for two different hydrodynamic diameters, 50 nm (the curves 2) and 60 nm (the curves 1) when the particles goes through Brownian relaxation. The particles are dispersed in water. Out of phase components for the respective particles show a maximum at the frequency corresponding to the Brownian relaxation period while the in phase components decline at that frequency.

In FIG. 3 there is also shown how the magnetic response will change in the frequency plane at different hydrodynamic volumes. In these calculations, thermally blocked magnetic coils and only one particle size have been assumed (in a real particle system we always have a certain size distribution), which will result in a somewhat wider magnetic response in the frequency plane but will not effect the present method. In the figure, one can see that when the hydrodynamic diameter increases, the magnetic response will shift downwards in frequency. By measuring this frequency shift, one can determine, for example if a certain bio-molecule has been attached to the surface (the hydrodynamic volume has thus increased) or if the interconnection between different bio-molecules has occurred. As the frequency shift depends on the size of the bio-molecules and the characteristic of their interaction with the surrounding fluid, it is also possible to determine the relative concentrations of respective bio-molecules or antibodies by studying the extent of the frequency shift.

Figure 1:
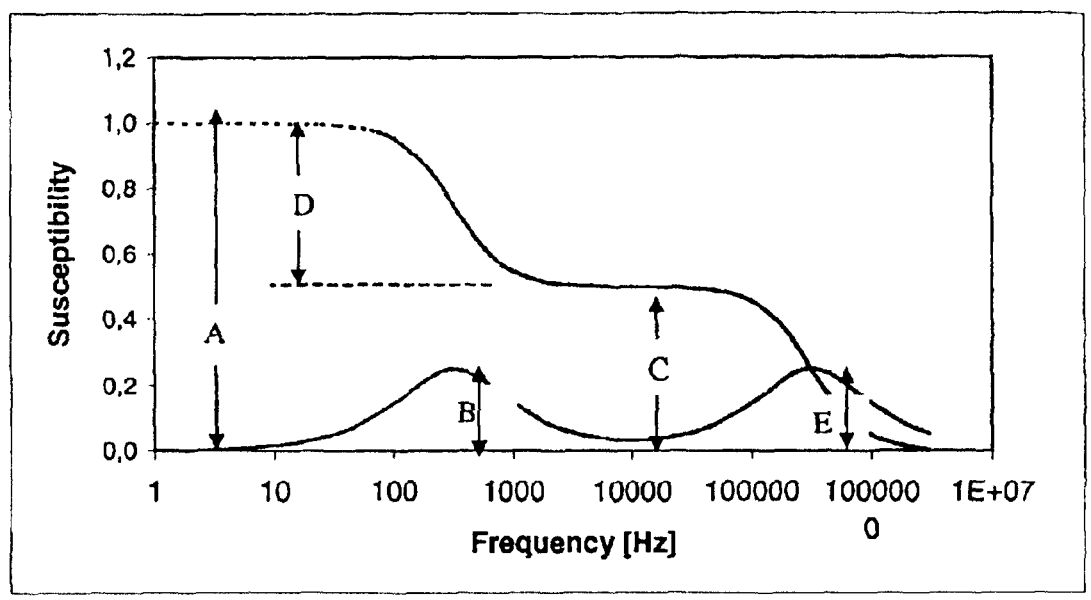
FIG. 1 shows the magnetic response as a function of frequency for a particle system exhibiting both Brownian and Néelian relaxation.

A known procedure is to detect both $\chi'$ and $\chi''$ over a broad frequency interval from some Hz to nearly some MHz for different (surface-) modifications and comparing these with each other (see FIGS. 1 and 3) via a subsequent consideration of the collected data. Another, often-used method of characterizing Brownian movement at a particle system is to study the response of the particles to an alternating magnetic field in the time domain: so-called relaxation time measurements. As the invention handles measurements in the frequency domain, we will avoid a closer description of measurement method at relaxation time measurements.

If the requirement is to examine the effect of particle modification (-modifications), the viscosity of the fluid should remain constant. Viscosity changes alter the Brownian movement of the particles, and also alter $\chi'$ and $\chi''$ frequency dependent. The influence of viscosity changes can therefore be difficult to separate from contributions caused by, among other things, particle modifications. On the other hand, the effect can be used for comparing different fluids viscosities when using identical particles but altering the fluid in question.

One method is to focus on the detection $\chi'$ and $\chi'$ at only one frequency, $f_{max}$, and at the same time determine $\delta f_{max}$, or at a few discreet frequency values. If required, a given particle system can be characterized separately, for example with respect to the degree of Brownian relaxation or the spreading size.

To make these methods work the particles must have a thermally blocked magnetic core (magnetic particle volume) which limit particle sizes and the magnetic anisotropy of the magnetic core.

A typical particle system suitable to use in this method is a particle with a magnetic core made of magnetite or maghemite with a diameter of about 20 nm. There are also other materials with particles exhibiting thermally blocked magnetization, for example Co doped ferric oxide or $CoFe_2O_4$ with a size of about 10 nm–15 nm, possibly rare earth metals, and others.

In many applications, especially those considered below, the magnetic core is covered with an external layer, for example a polymer like polyacrylamide or dextrane. Other covering materials can of course also occur, for example metal layers (like Au), other polymer, specific chemical compounds like silanes or thiols, and so on. It is often suitable to choose the thickness of the layer so that the total particle diameter varies from about 25 nm up to 1 μm (or higher).

To receive as large a percentage frequency change as possible at particle modifications, relatively small particles (about 50 nm) are used. It is assumed that if total sizes (diameters) from about 50 nm to 1 μm are used large enough percentage frequency changes are received with our method.

Figure 2:
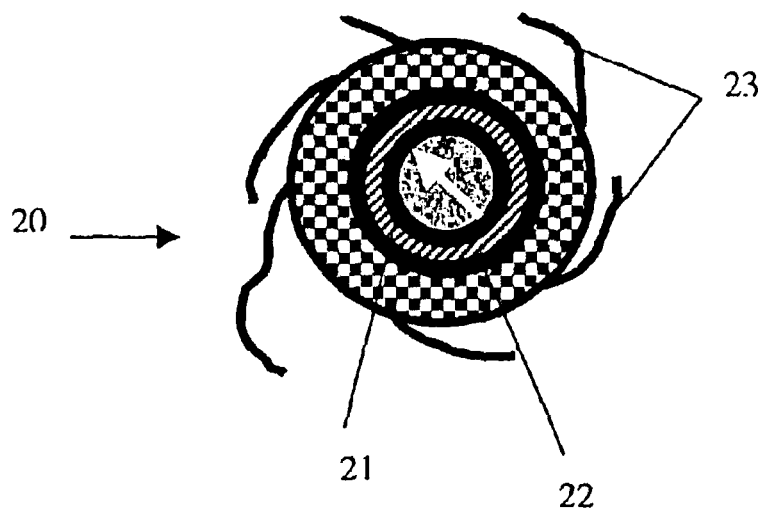
FIG. 2 shows schematically a section through a rotating magnetic particle with suitable intermediate layers and bio molecules.

FIG. 2 illustrates a magnetic core 20 covered with 2 extra layers 21, 22 that are rotating counterclockwise. The thick black lines shown in the figure between the different layers illustrates the intermediate surface material that can be differentiated from the material that makes up the bulk of the layer. To the external layer 22 long and thin bio-molecules 23 have been attached. The sketch of the particle illustrates a further important condition that the particle preparation should comply with: the material in the different layers are chosen so that the different layers are anchored to each other strongly enough (intermediate layer enthalpin bonding is high) so that they are prevented from rotating in proportion to each other when the external magnetic field is applied to the particle.

FIG. 3 shows how the in phase and out of phase component of the magnetic susceptibility vary with the frequency at room temperature for two different hydrodynamic diameters, 50 nm (the curves 2) and 60 nm (the curves 1) when the particles are going through Brownian relaxation. The particles are dispersed in water. The out of phase components for the respective particles show a maximum at the frequency corresponding to the Brownian relaxation period while in phase components decline at that frequency. How the magnetic response will change in the frequency plane at different hydrodynamic volumes is also shown in FIG. 3. In these calculations thermal blocked magnetic cores and only one particle size (in a real particle system, we always have a certain particle distribution) has been assumed, which will give a slightly broader magnetic response in the frequency plane but will not affect our method. In the figure one can see that when the hydrodynamic diameter increases the magnetic response will shift downwards in frequency. Through measuring this frequency shift one could determine if, for example, a certain molecule has bonded to the surface (the hydrodynamic volume has then increased) or if bonding of different bio-molecules have taken place. When the frequency shift depends on the sizes of bio-molecules and also the characteristic of their interaction with the surrounding fluid one could also determine the relative concentration of respective bio-molecules or antibodies through studying how large the frequency shift is.

A often used detection method is to detect the change in induced voltage for a double flushing system (detection flushing system) positioned in an excitation coil. The sample is placed in one of the detection coils. In this case a lock-in amplifying technique is used to measure the signal from the sample. This method is very sensitive and used in most commercial AC susceptometers. The frequency interval is typically from about 0.01 Hz up to 10 kHz. It is difficult to measure at higher frequencies with this measuring system. It is possible to measure up to slightly higher frequencies, for example 60 kHz, but this requires a specifically designed measurement system. To measure the susceptibility at yet higher frequencies, for example up to 10 MHz, a method based on detection of changes in inductance and resistance can be used for a toroid coil system with a soft magnetic material (for example mu-metal or some kind of ferrite material if high measuring frequencies are used). The sample is then placed in a thin gap in the magnetic toroid and one measures the circuit parameters of the toroid when the gap is empty and after placing the sample in the gap, respectively.

Figure 4:
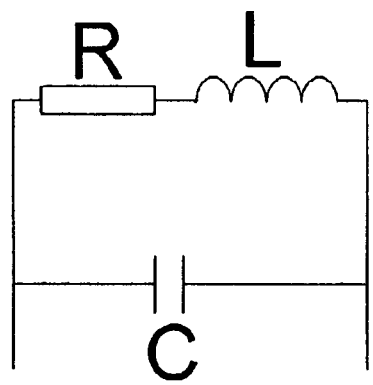
FIG. 4 shows the equivalent circuit of a coil.

Common for all these methods is that one can represent characteristics of a spiral wound coil with an equivalent electric circuit consisting of an inductance, L, in series with a resistance, R, (connected to a capacitance, C, in parallel with these—the capacitance depends on the electrical isolation of the wire and can often be neglected at lower frequencies, see FIG. 4) wherein the resistance and the inductance of the circuit can be changed when a magnetic sample is placed in the coil.

If a variable (AC) current $I(\omega t)$ (in phase with the AC magnetic field) is flowing in the circuit, it will induce a complex voltage in which the real part is in phase with the current while the imaginary part is out of phase in proportion to $I(\omega t)$.

Since, in the first place differences in the susceptibility are to be determined in the susceptibility that occurs at different particle preparations (or compare viscosities of two different fluids) a measure system is constructed differently measuring systems that are usually used. The measuring system 50, shown schematically in FIG. 5, consists of two identical detection coils 51, 52, surrounding two identical sample containers 53, 54 similar to commercially accessible. An excitation coil 55 which is intended to generate a homogeneous magnetic field at both sample containers surrounds the measuring coils and sample containers. The excitation coil, measuring coils and also sample containers are placed concentrically and also adjusted around the vertical center axis. Both respective sample positions and the respective measuring coil can be adjusted separately. There is no need of an excitation coil when using the two last-mentioned, alternative detection methods.

Figure 5:
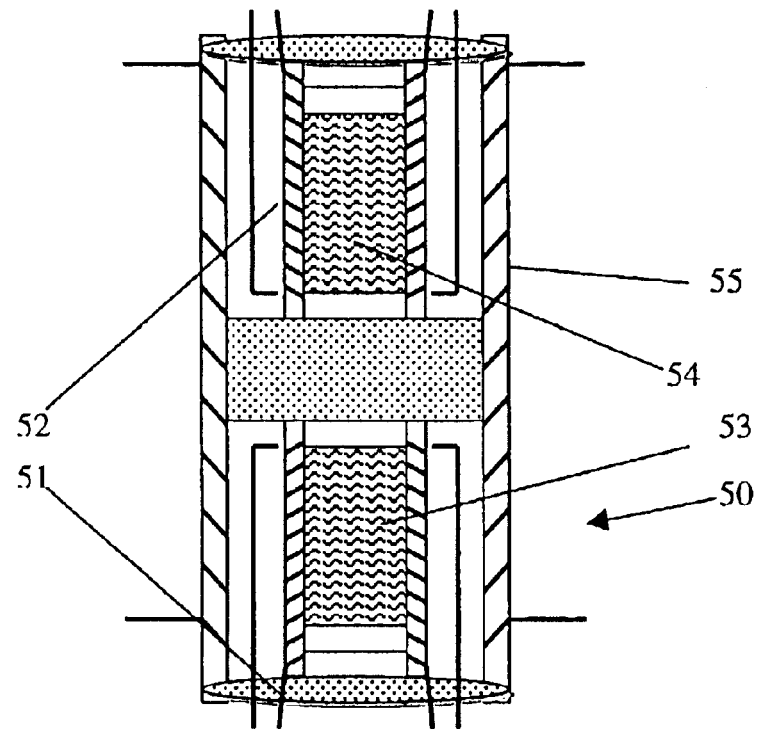
FIG. 5 shows schematically a section of an exemplary measuring system according to the invention.
Figure 12:
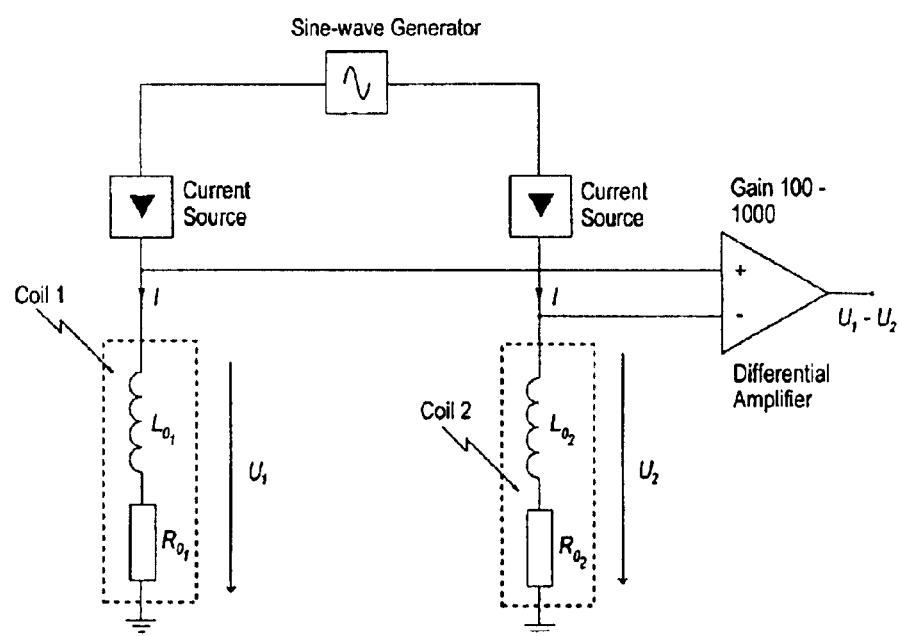
FIG. 12 is an alternative to the coupling of coils depicted in FIG. 7. Here, they are coupled in parallel with respect to each other in a suitable circuit.

The measuring system 50 in FIG. 5 comprises a separate excitation coil 55. However, it is not necessary and can be excluded from the construction. Thus, the measuring system will be simpler as it will comprise only two coils, both being fed by identical AC-current an example of a similar coupling where the coils are coupled in parallel is shown in FIG. 12. in this case, the excitation coils are removed from the measuring device 100 and only the coils 103 and 104 are used for both magnetization and detection.

The substantial advantages with the system of FIG. 5, whether or not the excitation coil is removed, is not only the possibility of comparative measuring but also the possibility of adjusting the system. The sensitivity of the measuring system is determined not only from the S/N state but also from the imbalance between two nominally identical partial systems containing sample container 1 (53) and sample container 2 (54) respectively with a detection coil each. The imbalance as measured without sample container or with identical sample container can occur for example as a result of:

Slightly different number of revolutions in respective detection coil.
In homogeneous magnetic field as a result of small tolerances when manufacturing concerning the placing of samples in relation to the detection coil and excitation coil respectively.

Different relative positions of the sample containers inside the detection coils.

Influence of manufacturing tolerances.

To reset (balance out) the difference in signal between the detection coils two methods can be used:

The system is constructed to make it possible to mechanically adjust the position of respective sample containers or, alternatively, change the position of respective detection coil slightly so that imbalance in the difference signal is minimized.

Figure 6:
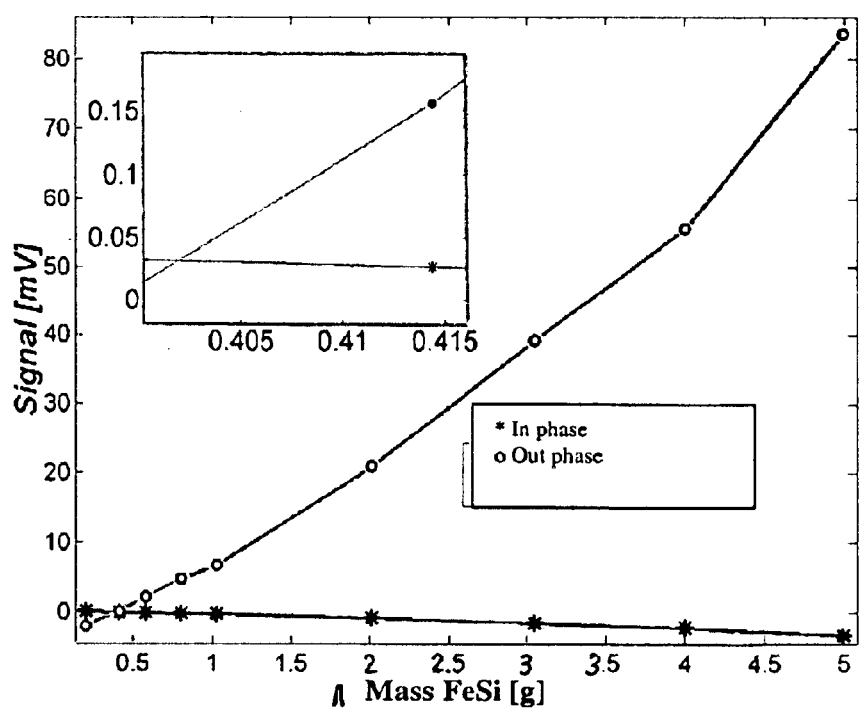
FIG. 6 shows adjustment of the measuring system according to the invention by means of adding a magnetic material showing $\chi'$=constant and $\chi''$=0, in the frequency interval used while measuring the Brownian relaxation.

The system is however constructed to balance the difference signal in a faster and simpler way, by providing a determined amount of dry magnetic particles (balls) in one of the spaces wherein the sample containers are placed (see FIGS. 5 and 6). The particles create an extra contribution to the original signal that can be adjusted in that way (set to zero). The dry magnetic particles do not show magnetic loss ($\chi''=0$) and also that the real part of the susceptibility is constant ($\chi'$=constant) in the examined frequency range.

There are a number of alternative detection methods:

Measuring Coils as a Feedback Element in an Oscillator Circuit

An alternative way of comparing two different preparations or modifications of the quantity of magnetic particles is to follow the frequency changes so induced by means of a oscillator system wherein the detection coils constitutes the frequency determining element in an oscillator circuit, for example, in the return coil (feedback circuit) of the oscillator. It is well known that the resonance frequency of such an oscillator is $f_{max}$, whereas its coil factor is a measure of $\delta f_{max}$, which is a measure of the energy losses (friction) of the particles. When the detection coils constitutes the frequency determining elements in the circuit, the resonance frequency will follow the changes of the L and R values of the coil, which occurs when the susceptibility of the particles is changed.

When detection of the AC difference between the coils is required i.e., comparison of two different particle systems (or two different fluids) the coils surrounding respective sample are electrically phase shifted towards each other so that the resonance frequency is determined from the difference between the inductance $\{\Delta L(=L_1-L_2)\}$ and resistance $\{\Delta R(=R_1-R_2)\}$ of the respective coils. One way to accomplish this using only passive components is to place coils in an AC bridge. Active components, for example OP amplifiers, can also be used, which involves simple subtraction of two voltages from each other. A conception how a suitable coupling can be constructed, can be obtained by observing FIG. 12. the difference in each potential over the coils 103 and 104 is achieved by means of the amplifier 105. if the output of the amplifier 108 is connected to the frequency generator 107 and the circuit is slightly modified, an oscillator is provided in which the coil is fed through the feedback through the current generators 106. Naturally, other circuit solution may be used; consequently the invention is not limited to the disclosed example.

The oscillator circuit can be shaped so that not only the frequency is detected but also changes in the total effect (or amplitude of the oscillators) to which the coil is exposed at different particle preparations: Frequency and dissipation will determine the effective changes of the circuit $\Delta L(=L_1-L_2)$ and $\Delta R(=R_1-R_2)$. These changes constitute a measure of changes of dissipation in the circuit. One can also determine an absolute measure of dissipation through measuring the decline of the oscillation when the coil is disconnected from the oscillator circuit.

By detecting changes in oscillator frequency and also the decline of signal amplitude from the oscillator system or effect changes (or amplitude changes) the response of the particles at a specific frequency, $f_{max}$ can be adjusted for the particle system used and also coil factor (energy losses) at the frequency can be determined.

The proceeding simplifies the measuring system when the need for a separate excitation coil vanishes.

Measuring Coils Driven by Means of a Frequency Generator

Figure 7:
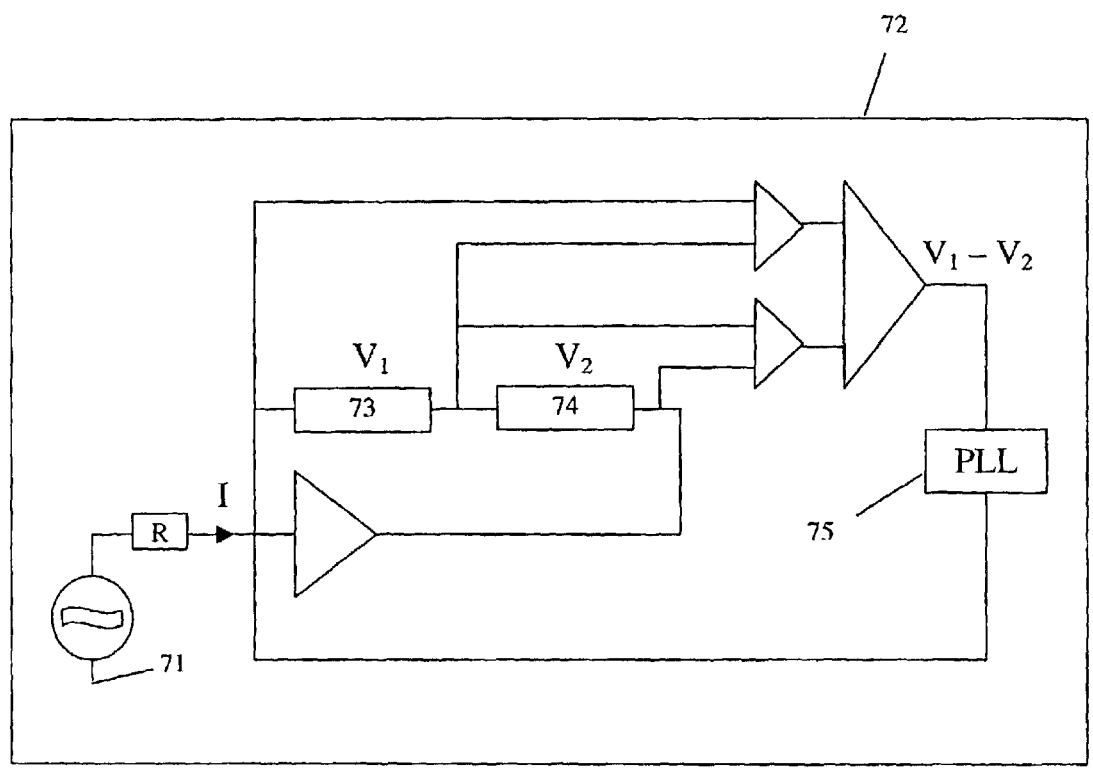
FIG. 7 shows schematically an alternative detection circuit (differential measurement without excitation coil) according to the invention.

Another measuring principle for detecting the wanted voltage difference is constructed from a phase lock (a so called Phase Lock Loop, PLL) according FIG. 7, which shows a principle sketch of an alternating detection circuit 70, wherein the coils 73 and 74 are connected in a series. A variable frequency generator, or alternatively a noise generator, 71 is used as an input signal and a measure of the complex voltage difference is achieved by means of a phase locked loop. The voltage difference is brought about by means of a suitable connection of the operation amplifier 72. A similar effect can be obtained when constructing an AC bridge as well wherein two of the four branches of the bridge constitutes of coil 73 and coil 74 respectively. Theoretically, the voltage difference is determined out of phase with 0° and 90° respectively in relation to the input signal. In practice, there is a certain extra phase displacement as a result of the operation amplifier. Once again, detection of the signal difference at one and the same frequency between the two detection coils is desired.

A possible principle for accomplishing the voltage difference according to the figure is by using an operation (instrument) amplifier in a suitable connection. Another possibility is based on placing respective coil in an AC bridge. The bridge is fed by an oscillator/frequency generator with a variable frequency at which the amplitude of the current flowing through the coils is held constant. The amplitude of the resulting voltage difference for a given phase displacement in relation to the input signal can be determined by means of a PLL circuit 75 (the phase difference is proportional to a DC voltage determined/generated by the PLL circuit). Together with the measuring of the amplitude of the signal an adequate description of the sample characteristics at a certain frequency is received. The advantages of the method is above all being able to measure the magnetic characteristics of the particle system over a relatively broad frequency interval and also that an excitation coil isn't needed.

In addition, the coupling according to FIG. 12 can be used in a similar way as the one illustrated in FIG. 7. The output is connected to a PLL-circuit, which senses the phase shift between the generated current from the current source 106 and the voltage difference at the output.

An alternative to using oscillator/frequency generator signals for generating time/period variable current is to excite the coils by means of white noise. The advantage is that one can receive frequency dependent information through a FFT filtration of the response without using frequency generator.

Figure 8:
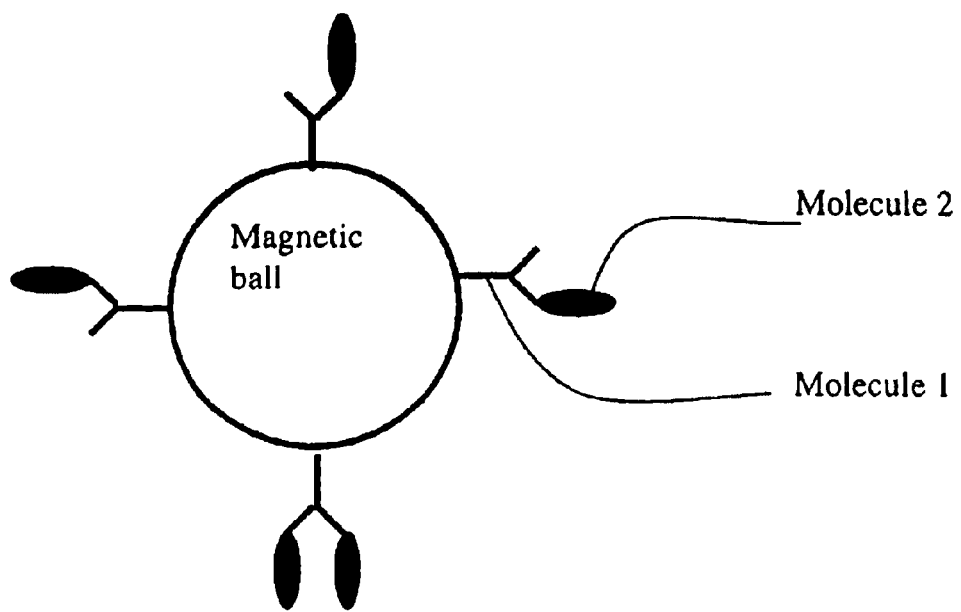
FIG. 8 shows schematically an application, according to the invention.
Figure 9:
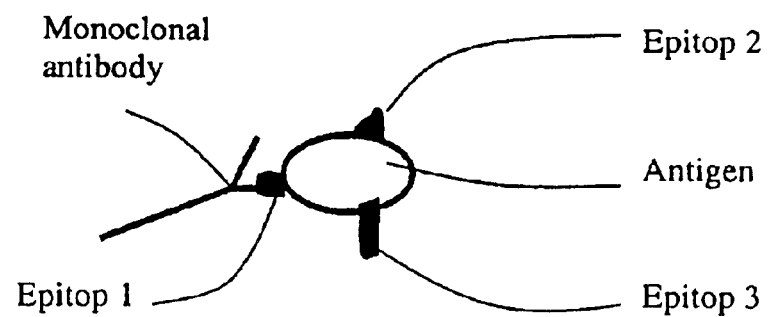
FIG. 9 shows a monoclonal antibody integrating with only one epitope on an antigen.
Figure 10:
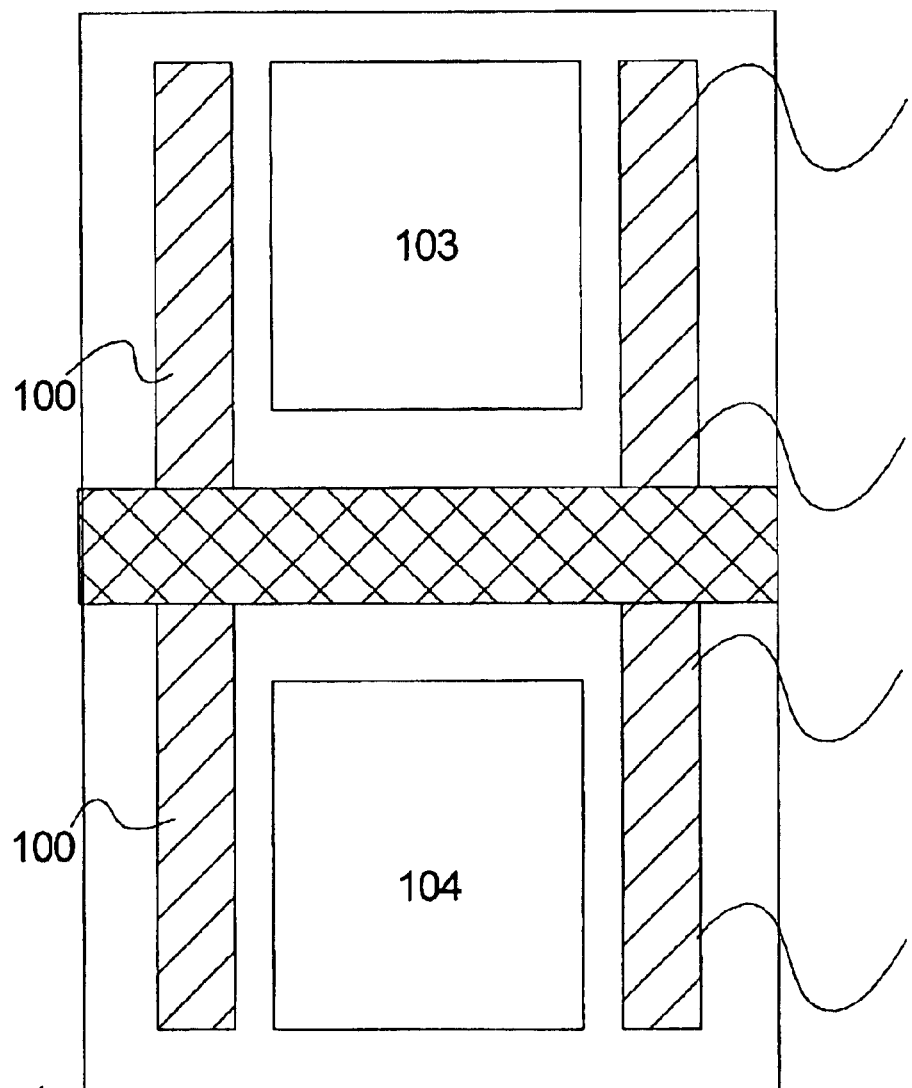
FIG. 10 is a schematic cross-section through a second exemplary measurement system according to the invention.

The described sensor is a general analysis instrument for analysis of different bio-molecules or other molecules in fluid. Examples of molecules to be analyzed can, for example, be proteins in a fluid solution, such as blood, blood plasma, serum, and urine. The method function on condition that the analysis (molecule 2) can be connected to the particle in some way, for example through specific interaction with another molecule (molecule 1) that before the beginning of the analysis has been connected to the ball, such as shown in FIG. 8. Observe that the dimensions (the size of the molecules in relation to the size of the ball) not are according to scale.

Figure 11:
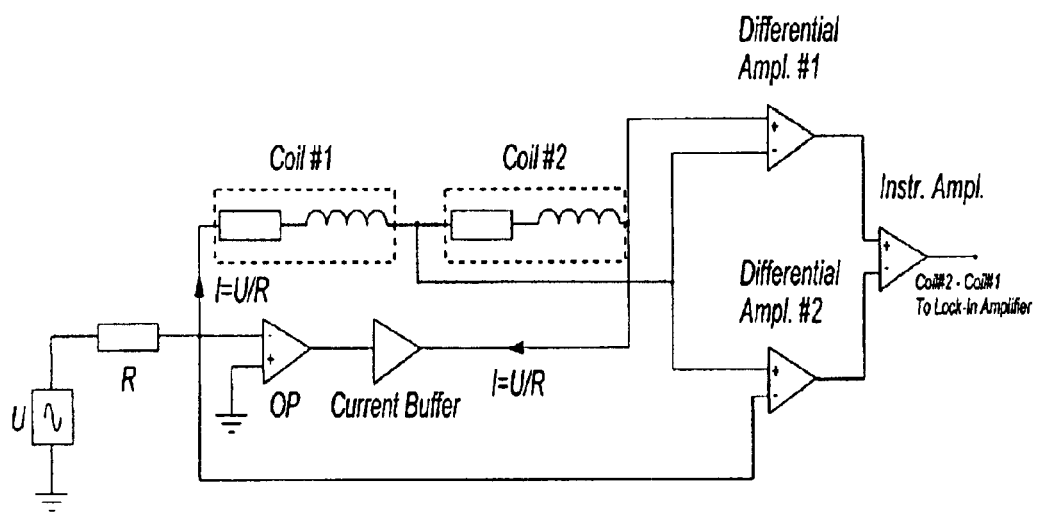
FIG. 11 is a schematic second alternative detection circuit (differential measuring without excitation coils) according to the invention.

Yet, another alternative to the coupling of FIG. 7 is illustrated in FIG. 11. In this coupling, a current buffer is arranged after the OP amplifier. The coils are denoted with "coil1" and "coil2". This coupling has the advantage of feeding two identical currents through the coils.

FIGS. 7 and 11 depict serially connected coils. In FIG. 12, the coils Coil1 and Coil2 are arranged in parallel. This allows a better measuring possibility where the signal-noise-ratio can be enhanced by directly measuring the differential signal from the two coils. The circuit comprises a sinus wave generator connected to two current sources. The output of each coil and also the input of each differential amplifier, the output signal of which is $U_1$-$U_2$, i.e. the voltage over the first and the second coil, respectively.

Since specific interactions usually occur in biological systems the sensor can probably play a significant role within this area, for example the analysis of biochemical markers for different diseases. Examples of molecules that can interact specific with each other are:

a) antibody-antigen
b) receptor-hormone
c) two complementary single strings of DNA
d) enzyme-substrate/enzyme-inhibitor The particle system (for example particle size and choice of molecule 1) is adapted according to size and type of molecule 2.

The sensor can for example be used within medical diagnostics. The new biosensor could, for example, replace some ELISA analysis (Enzyme Linked Immunosorbent Assay) analyses. This method is used today to a great extent to determine contents of biochemical markers (for example proteins) found in complex body fluids, such as blood, serum and cerebro-spinal fluid. Examples of ELISA analysis that can replace the new biosensor are:

a) analysis of tau proteins in cerebro-spinal fluid (part of diagnosis of Alzheimer's disease)
b) analysis of PSA in serum (diagnosis of prostate cancer)
c) analysis of acute phase proteins measured in connection with heart disease
d) analysis of CA 125 in serum (diagnosis of cancer in the ovaries)

It can be assumed that the sensor can be used for detection of several markers at the same time through using balls with different sizes and/or different materials in the same system. The different balls are covered with different "bio-molecule 1" (FIG. 8).

The new technique can be used for "low throughput screening", i.e., the accomplishment of one or several analysis at the same time, or for "high throughput screening", i,e, the accomplishment of a large number of analyses simultaneously. The latter can be accomplished by multiplying the sensor.

The invention is based on the use of magnetic particles. To make molecule 2 in the sample attach to the magnetic ball, the surface of the magnetic ball can be modified in a suitable way. This can be done, for example through covering the surface of the ball with dextrane, with alkanethiols with suitable end groups, with certain peptides and so on. On the dextrane surface (or other suitable intermediate layer) molecule 1, for example an antibody, can then be bonded by means of, for example, cyanobromide activation or carboxyl acid activation. When molecule 1 is connected to the magnetic ball, the balls are mixed with a sample to be analyzed, for example serum.

To determine presence of bio-molecules or antibodies in a carrier fluid containing magnetic particles with the suggested method, the following steps must be accomplished in the sample preparation, measuring and analysis of measuring data.

1. Mixing the magnetic particles with the sample to be analyzed with respect to a certain substance.
2. Filling a sample container with the sample prepared according to step 1.
3. Placing a sample container in the detection coils or detection system (depending on which equipment used for measuring the frequency dependents of the magnetic response).
4. Applying an external measure field over the sample with a certain amplitude and frequency.
5. Measuring the magnetic response (both in phase and out of phase components) at this frequency.
6. Changing frequency and performing a measurement according to steps 4 and 5.
7. The analysis of the result is to determine the Brownian relaxation period from in phase and out of phase components through using all data in the examined frequency interval (up to about 10 kHz). An alternative analysis could be merely determining how large the frequency shift is (for the same value of in phase and out of phase components) at a couple of different frequencies.

The system allows a quantitative comparison between different fluid viscosities. The viscosity can be measured analogous with what has been described as to the rest of the invention, with the difference that identical particle are used for viscosity measuring. Frequency changes occur as a result of different viscosities. It is not only the resonance frequency, $f_{max}$, that will be changed but also $\delta\ f_{max}$. The advantage of the method compared with other ways of measuring the viscosity is:

relatively small fluid amounts is needed
the possibility to measure viscosity locally round the particle, which make detection of viscosity gradients in a fluid volume possible This viscosity detection method is however based on the particles still being stable in the different fluids.

The invention is not limited to the shown and described embodiments. However modifications, changes and differences within the scoop of the enclosed claims are also possible.

What we claim is:

1. A method for detecting changes of magnetic response of at least one magnetic particle provided with an external layer in a carrier fluid, the method comprising:

using a measuring procedure comprising measuring the characteristic rotation time of said magnetic particle with respect to said external layer, said measuring procedure further involving measuring Brownian relaxation in said carrier fluid under influence of an external alternating magnetic field; and measuring a change in a hydrodynamic volume of the particle changes upon modification of an effective volume of the particle or its interaction with the carrier fluid, resulting in a change of a frequency ($f_{max}$) where an out of phase component of a magnetic susceptibility has its maximum.

2. The method of claim 1, wherein said measuring procedure further involves measuring at least one of in-phase or out-phase components of the magnetic susceptibility in a frequency range.

3. The method of claim 1, wherein said measuring procedure comprises a relative measurement, whereby changes in a modified particle system are compared with an original system.

4. The method of claim 3, wherein at least two sample containers and two detector coils are used.

5. The method of claim 4, wherein an oscillator circuit is used at first frequency, being a resonant frequency, and wherein detector coils are placed as a frequency determining element in the oscillating circuit so that they are out of phase with each other.

6. The method of claim 5, comprising measuring the frequency and/or an effect or amplitude of oscillations from the oscillating circuit over the coils.

7. The method of claim 4, comprising arranging an external oscillator-/frequency generator, placing said detector coils in an alternating bridge so that a difference between both detector coils is measured, and measuring a phase difference between an out signal, being one of a current and/or voltage, of the frequency generator and a signal, being one of a current or voltage, over the bridge.

8. The method of claim 7, wherein a difference in amplitude between the out signal of the oscillator or frequency generator is measured and compared with an amplitude of the signal in the bridge.

9. The method of claim 8, wherein the measurement is accomplished at one or several different frequencies.

10. The method of claim 3, wherein a noise source is used and a response of the system is analyzed by means of a FFT (Fast Fourier Transform) analysis of an output signal.

11. The method of claim 3, wherein a signal difference between said coils is set to zero.

12. The method of claim 11, wherein said zero setting is obtained through mechanically adjusting the position of each sample container or alternatively changing the position of each detector coil so that the signal difference is minimized.

13. The method of claim 11, wherein said zero-setting is obtained through minimizing the signal by feeding a defined amount of a magnetic substance in a space comprising the sample containers, so that the substance creates an extra contribution to the original signal, which can be set to zero there through.

14. The method of claim 13, wherein said magnetic substance shows substantially zero magnetic loss (imaginary part=0) and that a real part of susceptibility is constant in the examined frequency range.

15. The method of claims 1, wherein the method is used in the analysis instrument for analysis of different biomolecules or other molecules in a fluid.

16. The method of claim 15, wherein said molecules, comprises one or several of proteins in a fluid solution, such as blood, blood plasma, serum and urine.

17. The method of claim 15, wherein said analysis comprising a first molecule is connected to said particle through interaction with a second molecule.

18. The method of claim 15, wherein molecules that specifically can be integrated with each other comprises one or more antibody-antigen pairs, receptor-hormone pairs, two complementary single DNA strings, enzymes-substrate pairs, or enzyme-inhibitor pairs.

19. The method of claim 1, wherein the surface of the magnetic particle is modified through covering the surface with one or several of dextranes, with alkanethiols, with suitable end-groups or with certain peptides.

20. The method of claim 19, comprising bonding a first molecule to a dextrane surface using one of a cyanobromid activation or with carboxyl acid activation.

21. A device for detecting changes of magnetic response with at least one magnetic particle provided with an external layer in a carrier fluid, said detection comprising measuring said magnetic particles characteristic rotation period with respect to effect of said external layer, and said measurement involving measurement of a Brownian relaxation in said carrier fluid under influence of an external alternating magnetic field, said device comprising means for generating said alternating magnetic field, at least two substantially identical detection coils connected to detection electronics and sample containers for absorbing carrier fluid, means for measuring a change in the frequency ($f_{max}$), where an out of phase component of a magnetic susceptibility has its maximum at modification of the effective volume of the particle or its interaction with said carrier fluid when a hydrodynamic volume of said particle is changed.

22. The device of claim 21, wherein said excitation coil surrounds detection coils and sample containers for generation of a homogeneous magnetic field by said sample container.

23. The device of claim 22, wherein said excitation coil, measuring coils and sample containers are placed concentric and adjusted around their vertical center axis.

24. The device of claim 22, comprising an oscillator system wherein the detection coils forms a frequency determining element in an oscillator circuit.

25. The device of claim 21, wherein said coils are arranged in the return coil of the oscillator.

26. The device of claim 21, wherein said coils are arranged as excitation coils.

27. The device of claim 21, wherein said coils surrounding each sample are electrically phase shifted versus each other so that the resonance frequency is determined from the difference between the inductance and resistance, respectively, of the coil.

28. The device of claim 21, wherein said coils are placed in an AC-bridge.

29. The device of claim 27, comprising an op-amplifier for subtraction of two voltages from each other.

30. The device of claim 21, comprising a phase-lock circuit.

31. The device of claim 21, comprising an oscillator/frequency generator signals for generating time variable current for exciting the coils by means of white noise.

32. The device of claim 21, wherein frequency depending information is received through FFT-filtering of response.

33. The device of claim 21, wherein the measurement over the coils is in series or parallel.

34. The device of claim 21, comprising a circuit comprising a sinus wave generator connected to two current sources, the output of each current source being connected to each one end of each coil and also the input of a differential amplifier, having an output being the voltage difference over the first and the second coils.

35. The device of claim 21, further comprising a noise source and that the response of the device is analyzed using a FFT (Fast Fourier Transform) analyze of one of output signals.

36. A method for determining an amount of molecules in a carrier fluid containing magnetic particles, the method comprising the steps of:
  A. providing particles with a layer, which interacts or reacts with the substance to be analyzed,
  B. mixing the magnetic particles with the sample to be analyzed regarding molecules,
  C. filling a sample container with fluid being prepared according to B,
  D. placing a sample container in the detection system,
  E. applying an external measurement field over the sample with a certain amplitude and frequency, F. measuring the magnetic response, both the in phase and out of phase components, at this frequency, G. changing frequency and performing measurement again according to D and E, H. analyzing the result through determining a Brownian relaxation time from in phase and out of phase components by using data in the examined frequency interval.

37. The method of claim 36, further comprising determining the frequency shift for the same value of in phase and out of phase component at different frequencies.

38. The method of claim 36 or 37, wherein said molecules consist of a bio-molecule.

39. A method for detecting changes of magnetic response of at least one magnetic particle provided with an external layer in a carrier fluid, the method comprising:

using a measuring procedure comprising measuring the characteristic rotation time of said magnetic particle with respect to said external layer, and measuring Brownian relaxation in said carrier fluid under the influence of an external alternating magnetic field, upon modification of the effective volume of the particle or its interaction with the carrier fluid a hydrodynamic volume of the particle changes, measuring a change of the frequency ($f_{max}$) where an out of phase component of the magnetic susceptibility has its maximum.

40. The method of claim 39, wherein said measuring procedure further involves measuring at least one of in-phase or out-phase components of the magnetic susceptibility in a frequency range.

41. The method of claim 39, wherein said measuring procedure comprises a relative measurement, whereby changes in a modified particle system are compared with an original system.

42. The method of claim 41, wherein at least two sample containers and two detector coils are used.

43. The method of claim 42, wherein an oscillator circuit is used at first frequency, being a resonant frequency, and wherein detector coils are placed as a frequency determining element in the oscillating circuit so that they are out of phase with each other.

44. The method of claim 43, comprising measuring the frequency and/or an effect or amplitude of oscillations from the oscillating circuit over the coils.

45. The method of claim 41, comprising arranging an external oscillator-/frequency generator, placing said detector coils in an alternating bridge so that a difference between both detector coils is measured, and measuring a phase difference between an out signal, being one of a current and/or voltage, of the frequency generator and a signal, being one of a current or voltage, over the bridge.

46. The method of claim 45, wherein a difference in amplitude between the out signal of the oscillator or frequency generator is measured and compared with an amplitude of the signal in the bridge.

47. The method of claim 46, wherein the measurement is accomplished at one or several different frequencies.

48. The method of claim 41, wherein a noise source is used and a response of the system is analyzed by means of a FFT (Fast Fourier Transform) analysis of an output signal.

49. The method of claim 41, wherein a signal difference between said coils is set to zero.

50. The method of claim 49, wherein said zero setting is obtained through mechanically adjusting the position of each sample container alternatively changing the position of each detector coil so that the signal difference is minimized.

51. The method of claim 49, wherein said zero-setting is obtained through minimizing the signal by feeding a defined amount of a magnetic substance in a space comprising the sample containers, so that the substance creates an extra contribution to the original signal, which can be set to zero there through.

52. The method of claim 51, wherein said magnetic substance shows substantially zero magnetic loss (imaginary part =0) and that a real part of susceptibility is constant in the examined frequency range.

53. The method of claim 39, wherein the method is used in the analysis instrument for analysis of different bio-molecules or other molecules in a fluid.

54. The method of claim 53, wherein said molecules, comprise one or several of proteins in a fluid solution, such as blood, blood plasma, serum and urine.

55. The method of claim 53, wherein said analysis comprising a first molecule is connected to said particle through interaction with a second molecule.

56. The method of claim 53, wherein molecules that specifically can be integrated with each other comprise one or more antibody-antigen pairs, receptor-hormone pairs, two complementary single DNA strings, enzymes-substrate pairs, or enzyme-inhibitor pairs.

57. The method of claim 39, wherein the surface of the magnetic particle is modified through covering the surface with one or several of dextranes, with alkanethiols, with suitable end-groups or with certain peptides.

58. The method of claim 57, comprising bonding a first molecule to a dextrane surface, using one of a cyanobromid activation or with carboxyl acid activation.

* * * * *